United States Patent [19]

Traxler

[11] 4,452,792
[45] Jun. 5, 1984

[54] ACRIDINE SUBSTITUTED PHOSPHORUS COMPOUNDS AND THEIR INSECTICIDAL USE

[75] Inventor: James T. Traxler, Evanston, Ill.

[73] Assignee: Velsicol Chemical Corporation, Chicago, Ill.

[21] Appl. No.: 453,643

[22] Filed: Dec. 27, 1982

[51] Int. Cl.³ .................. A01N 43/42; C07D 487/00
[52] U.S. Cl. ........................................ 424/200; 546/23
[58] Field of Search .......................... 546/23; 424/200

[56] References Cited
U.S. PATENT DOCUMENTS
4,404,220 9/1983 Traxler ............................. 424/275

Primary Examiner—Alan L. Rotman
Attorney, Agent, or Firm—Robert J. Schwarz

[57] ABSTRACT

This invention discloses new insecticidal chemical compounds of the following formula and their use in controlling insects:

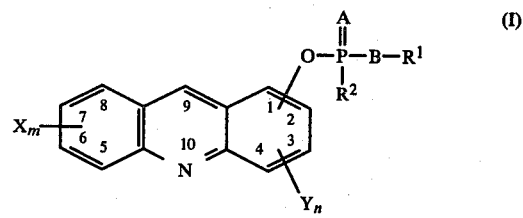

wherein X and Y are each independently selected from the group consisting of halogen, alkyl, haloalkyl, nitro, alkylsulfinyl, alkylsulfonyl and cyano; m and n are integers from 0 to 3; $R^1$ is selected from the group consisting of alkyl and

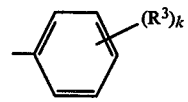

wherein $R^3$ is selected from the group consisting of halogen, alkyl, haloalkyl, nitro and cyano; and k is an integer from 0 to 3; $R^2$ is selected from the group consisting of alkyl, alkoxy, alkylthio, amino, alkylamino, dialkylamino and

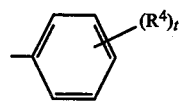

wherein $R^4$ is selected from the group consisting of halogen, alkyl, haloalkyl, nitro and cyano; and t is an integer from 0 to 3; and A and B are each independently selected from the group consisting of oxygen and sulfur.

10 Claims, No Drawings

ACRIDINE SUBSTITUTED PHOSPHORUS COMPOUNDS AND THEIR INSECTICIDAL USE

This invention relates to new compositions of matter and more specifically relates to new chemical compounds of the formula

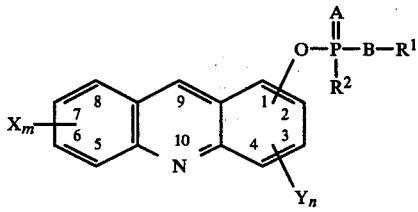 (I)

wherein X and Y are each independently selected from the group consisting of halogen, alkyl, haloalkyl, nitro, alkylsulfinyl, alkylsulfonyl and cyano; m and n are integers from 0 to 3; $R^1$ is selected from the group consisting of alkyl and

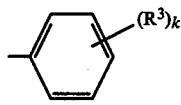

wherein $R^3$ is selected from the group consisting of halogen, alkyl, haloalkyl, nitro and cyano; and k is an integer from 0 to 3; $R^2$ is selected from the group consisting of alkyl, alkoxy, alkylthio, amino, alkylamino, dialkylamino and

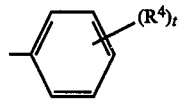

wherein $R^4$ is selected from the group consisting of halogen, alkyl, haloalkyl, nitro and cyano; and t is an integer from 0 to 3; and A and B are each independently selected from the group consisting of oxygen and sulfur.

The compounds of the present invention are useful as insecticides. In a preferred embodiment of the present invention X and Y are independently selected from the group consisting of halogen, lower alkyl, lower haloalkyl, nitro, lower alkylsulfinyl, lower alkylsulfonyl and cyano; m and n are integers from 0 to 3; $R^1$ is selected from the group consisting of lower alkyl and

wherein $R^3$ is selected from the group consisting of halogen, lower alkyl, lower haloalkyl, nitro and cyano; and k is an integer from 0 to 3; $R^2$ is selected from the group consisting of lower alkyl, lower alkoxy, lower alkylthio, amino, lower alkylamino, di(lower alkyl)amino, and

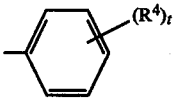

wherein $R^4$ is selected from the group consisting of halogen, lower alkyl, lower haloalkyl, nitro and cyano; t is an integer from 0 to 3; and A and B are each independently selected from the group consisting of oxygen and sulfur.

The term lower as used herein designates a straight or branched carbon chain of up to six carbon atoms.

The compounds of the present invention can be prepared by reacting a compound of the formula

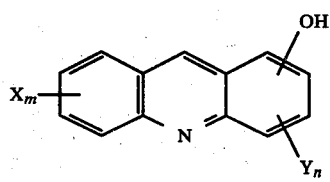 (II)

wherein X, Y, m and n are as heretofore described, with a phosphorus compound of the formula

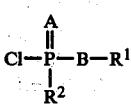 (III)

wherein A, B, $R^1$ and $R^2$ are as heretofore described. This reaction can be effected by combining the compounds of formulae II and III in an inert organic reaction medium such as toluene or methylene chloride in the presence of an acid acceptor such as tertiary amine. The reactants are typically combined with agitation at temperatures ranging from $-20°$ C. to ambient temperatures. The reaction mixture can be stirred for a period of several hours to insure completeness of the reaction. The acid acceptor salt can then be removed by filtration and/or washing with water and the remaining mixture stripped of solvent to yield the desired product. This product can then be used as such or can be further purified by standard techniques.

The compounds of formulae II and III are known in the art. Due to instability some of the compounds of formula III can be prepared shortly before their use in reacting with the compound of formula II. This preparation can be effected by reacting a phosphorodichloride of the formula

 (IV)

wherein A and $R^2$ are as heretofore described, with an alcohol of the formula

 (V)

H—B—$R^2$ wherein B and $R^2$ are as heretofore described. This reaction can be readily carried out by combining equimolar amounts of the compounds of formulae IV and V in an inert organic solvent such as toluene in the presence of an acid acceptor such as a tertiary amine. This reaction can be carried out at lower temperatures such as those ranging from −40° C. to 10° C. The reaction product mixture can then be used directly for reaction with the compound of formula II or the product can be isolated first by conventional means.

Exemplary acridines of formula II useful in preparing the compounds of the present invention include: 1-hydroxyacridine, 2-hydroxyacridine, 3-hydroxyacridine, 4-hydroxyacridine, 2-hydroxy-7-chloroacridine, 3-hydroxy-7-bromoacridine, 2-hydroxy-5-methylacridine, 4-hydroxy-8-nitroacridine, 3-hydroxy-7-chloromethylacridine, 2-hydroxy-6-trifluoromethylacridine, 2-hydroxy-5-methylsulfinylacridine, 3-hydroxy-5-methylsulfonylacridine, 2-hydroxy-6-cyanoacridine and the like.

Exemplary compounds of formula III suitable for preparing the compounds of the present invention are O-ethyl S-propyl phosphorochloridothiolate; O-ethyl S-propyl phosphorochloridothiolothioate; O-(2,4-dicyanophenyl) S-propyl phosphorochloridothiolate; O-(3,4,5-trichlorophenyl) S-propyl phosphorochloridothiolothionate; S-ethyl S-propyl phosphorochloridothiolate; S-butyl S-pentyl phosphorochloridodithiolothionate; S-pentyl ethylphosphonochloridothioate; S-(3-nitrophenyl) (3-chlorophenyl) phosphonochloridothiolothioate; O-(2,3-dimethylphenyl) S-butyl phosphorochloridothiolate; O-ethyl O-butyl phosphorochloridothionate; O-(4-chloro-5-methylphenyl) O-propyl phosphorochloridothionate; O-ethyl S-propyl phosphorochloridothiolothionate; O-ethyl ethylphosphonochloridothiolate; O-ethyl N,N-dimethylphosphoramidochloridate; S-propyl N,N-diethylphosphoramidochloridothiolate; S-pentyl N,N-dihexylphosphoramidothiolothionate; O-butyl N-butylphosphoramidochloridate; S-hexyl phosphoramidochloridothiolate and the like.

The manner in which the compounds of the present invention can be prepared is more specifically illustrated in the following examples.

EXAMPLE 1

Preparation of O-Ethyl O-Acridin-2-yl S-Propyl Phosphorothioate

2-Hydroxyacridine (1.90 grams; 0.01 mole), triethylamine (1.01 grams; 0.01 mole), tetrahydrofuran (30 ml) and toluene (20 ml) were charged into a glass reaction vessel equipped with a mechanical stirrer and thermometer. The mixture was cooled to about 0° C. and O-ethyl S-propyl phosphorochloridothioate (2.01 grams; 0.01 mole) dissolved in toluene (23 ml) was added with stirring over a period of about 20 minutes. After the addition was completed stirring was continued for 3 hours allowing the mixture to warm up to room temperature. Stirring was continued overnight. After this time the reaction mixture was filtered to remove triethylamine hydrochloride. The filtrate was washed, treated with charcoal and stripped of solvent leaving yellow/green oil as the residue. This residue was subjected to flash chromatography using ethyl acetate as the eluant to yield the desired product O-ethyl O-acridin-2-yl S-propyl phosphorothioate as a yellow brown oil.

EXAMPLE 2

Preparation of O-Ethyl O-3-Chloroacridin-2-yl S-Propyl Phosphorothioate

2-Hydroxyacridine (3.17 grams; 0.015 mole) and acetic acid (100 ml) are charged into a glass reaction vessel equipped with a stirrer and thermometer. The mixture is cooled to 15° C. and a solution of chlorine (0.015 mole) in acetic acid (25 ml) is added dropwise with stirring. After the addition is completed stirring is continued at room temperature overnight. After this time the reaction mixture is filtered to recover product. The product is then washed, dried and dissolved in tetrahydrofuran (50 ml). The solution is treated with triethylamine (2 ml). The treated solution is then filtered and the filtrate treated with activated charcoal. The filtrate is then stripped of solvent in a rotary evaporator to yield chloro-2-hydroxyacridine.

The acridine prepared above and triethylamine (1.4 ml) are charged into a glass reaction vessel equipped with a stirrer and thermometer. To this is added a cooled solution (0° C.) of O-ethyl S-propyl phosphorochloridothioate (0.01 mole) in toluene (25 ml). The mixture is stirred with continued cooling for ½ hour and thereafter at room temperature overnight. After this time the reaction mixture is filtered to remove triethylamine hydrochloride and the filtrate is stripped of solvent in a rotary evaporator leaving a residue. This residue is subjected to flash chromatography using ethyl acetate as the eluant to yield the desired product.

EXAMPLE 3

Preparation of O-Methyl O-(4-Chloroacridin-2-yl) S-Propyl Phosphorothioate

2-Hydroxy-4-chloroacridine (0.01 mole), triethylamine (0.01 mole) tetrahydrofuran (25 ml) and toluene (25 ml) are charged into a glass reaction vessel equipped with a mechanical stirrer and thermometer. The mixture is cooled to a temperature of about 0° C. and O-methyl S-propyl phosphorochloridothioate (0.01 mole) dissolved in toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then washed with water, dried over anhydrous magnesium sulfate and stripped of solvents leaving a residue. This residue is subjected to flash chromatography using ethyl acetate as the eluant to yield the desired product O-methyl O-(4-chloroacridin-2-yl) S-propyl phosphorothioate.

EXAMPLE 4

Preparation of O,O-Diethyl O-(4-Methylacridin-2-yl) Phosphate

2-Hydroxy-4-methylacridine (0.01 mole), triethylamine (0.01 mole) tetrahydrofuran (25 ml) and toluene (25 ml) are charged into a glass reaction vessel equipped with a mechanical stirrer and thermometer. The mixture is cooled to a temperature of about 0° C. and O,O-diethyl chloridophosphate (0.01 mole) dissolved in toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then washed with water, dried over anhydrous magnesium sulfate and stripped of solvents leaving a residue. This residue is subjected to flash chromatography using ethyl acetate as the eluant to yield the desired product O,O-diethyl (O-(4-methylacridin-2-yl) phosphate.

EXAMPLE 5

Preparation of O-(3-Chlorophenyl) O-(4,6-Dichloroacridin-2-yl) Methylphosphonate 2-Hydroxy-4,6-dichloroacridine (0.01 mole), triethylamine (0.01 mole), tetrahydrofuran (25 ml) and toluene (25 ml) are charged into a glass reaction vessel equipped with a mechanical stirrer and thermometer. The mixture is cooled to a temperature of about 0° C. and O-(3-chlorophenyl) methylchloridophosphonate (0.01 mole) dissolved in toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then washed with water, dried over anhydrous magnesium sulfate and stripped of solvents leaving a residue. This residue is subjected to flash chromatography using ethyl acetate as the eluant to yield the desired product O-(3-chlorophenyl) O-(4,6-dichloroacridin-2-yl) methylphosphonate.

EXAMPLE 6

Preparation of O,S-Diethyl O-(2-Bromo-6-methylacridin-4-yl) Phosphorodithioate

2-Bromo-4-hydroxyacridine (0.01 mole), triethylamine (0.01 mole), tetrahydrofuran (25 ml) and toluene (25 ml) are charged into a glass reaction vessel equipped with a mechanical stirrer and thermometer. The mixture is cooled to a temperature of about 0° C. and O,S-diethyl phosphorochloridodithioate (0.01 mole) dissolved in toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then washed with water, dried over anhydrous magnesium sulfate and stripped of solvents leaving a residue. This residue is subjected to flash chromatography using ethyl acetate as the eluant to yield the desired product O,S-diethyl O-(2-bromo-6-methylacridin-4-yl) phosphorodithioate.

EXAMPLE 7

Preparation of O-(2,4-Diethylphenyl) O-(6-Trifluoromethylacridin-3-yl) S-Propyl Phosphorothioate 3-Hydroxy-6-trifluoromethylacridine (0.01 mole), triethylamine (0.01 mole), tetrahydrofuran (25 ml) and toluene (25 ml) are charged into a glass reaction vessel equipped with a mechanical stirrer and thermometer. The mixture is cooled to a temperature of about 0° C. and O-(2,4-dimethylphenyl) S-propyl phosphorochloridothioate (0.01 mole) dissolved in toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then washed with water, dried over anhydrous magnesium sulfate and stripped of solvents leaving a residue. This residue is subjected to flash chromatography using ethyl acetate as the eluant to yield the desired product O-(2,4-dimethylphenyl) O-(6-trifluoromethylacridin-3-yl) S-propyl phosphorothioate.

EXAMPLE 8

Preparation of O-(4-Trifluoromethylphenyl) O-(4-Nitroacridin-1-yl) S-Butyl Phosphorothioate 1-Hydroxy-4-nitroacridine (0.01 mole), triethylamine (0.01 mole) tetrahydrofuran (25 ml) and toluene (25 ml) are charged into a glass reaction vessel equipped with a mechanical stirrer and thermometer. The mixture is cooled to a temperature of about 0° C. and O-(4-trifluoromethylphenyl) S-butyl phosphorochloridothioate (0.01 mole) dissolved in toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then washed with water, dried over anhydrous magnesium sulfate and stripped of solvents leaving a residue. This residue is subjected to flash chromatography using ethyl acetate as the eluant to yield the desired product O-(4-trifluoromethylphenyl) O-(4-nitroacridin-1-yl) S-butyl phosphorothioate.

EXAMPLE 9

Preparation of O-(4-Nitrophenyl) O-(4-trifluoromethylacridin-2-yl) S-Ethyl Phosphorothioate 2-Hydroxy-4-trifluoromethylacridine (0.01 mole), triethylamine (0.01 mole), tetrahydrofuran (25 ml) are charged into a glass reaction vessel equipped with a mechanical stirrer and thermometer. The mixture is cooled to a temperature of about 0° C. and O-(4-nitrophenyl) S-ethyl phosphorochloridothioate (0.01 mole) dissolved in toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then washed with water, dried over anhydrous magnesium sulfate and stripped of solvents leaving a residue. This residue is subjected to flash chromatography using ethyl acetate as the eluant to yield the desired product O-(4-nitrophenyl) O-(4-trifluoromethylacridin-2-yl) S-ethyl phosphorothioate.

EXAMPLE 10

Preparation of S-(4-Cyanophenyl) O-(7-Nitroacridin-2-yl) S-Propyl Phosphorodithioate 2-Hydroxy-7-nitroacridine (0.01 mole), triethylamine (0.01 mole), tetrahydrofuran (25 ml) and toluene (25 ml) are charged into a glass reaction vessel equipped with a mechanical stirrer and thermometer. The mixture is cooled to a temperature of about 0° C. and S-(4-cyanophenyl) S-propyl phosphorochloridodithioate (0.01 mole) dissolved to toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then washed with water, dried over anhydrous magnesium sulfate and stripped of solvents leaving a residue. This residue is subjected to flash chromatography using ethyl acetate as the eluant to yield the desired product S-(4-cyanophenyl) O-(7-nitroacridin-2-yl) S-propyl phosphorodithioate.

EXAMPLE 11

Preparation of O-(2-Methyl-4,6-dichlorophenyl) O-(3-Methylsulfinyl-7-cyanoacridin-1-yl) S-Propyl Phosphorothioate 1-Hydroxy-3-methylsulfinyl-7-cyanoacridine (0.01 mole), triethylamine (0.01 mole), tetrahydrofuran (25 ml) and toluene (25 ml) are charged into a glass reaction vessel equipped with a mechanical stirrer and thermometer. The mixture is cooled to a temperature of about 0° C. and O-(2-methyl-4,6-dichlorophenyl) S-propyl phosphorochloridothioate (0.01 mole) dissolved in toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then washed with water, dried over anhydrous magnesium sulfate and stripped of solvents leaving a residue. This residue is subjected to flash chromatography using ethyl acetate as the eluant to yield the desired product O-(2-methyl-4,6-dichlorophenyl) O-(3-methylsulfinyl-7-cyanoacridin-1-yl) S-propyl phosphorothioate.

EXAMPLE 12

Preparation of O-(3-Bromophenyl) O-(4-Cyano-6-methylsulfonylacridin-2-yl) S-Phenyl Phosphorothioate 2-Hydroxy-4-cyano-6-methylsulfonylacridine (0.01 mole), triethylamine (0.01 mole), tetrahydrofuran (25 ml) and toluene (25 ml) are charged into a glass reaction vessel equipped with a mechanical stirrer and thermometer. The mixture is cooled to a temperature of about 0° C. and O-(3-bromophenyl) S-phenyl phosphorochloridothioate (0.01 mole) dissolved in toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then wasshed with water, dried over anhydrous magnesium sulfate and stripped of solvents leaving a residue. This residue is subjected to flash chromatography using ethyl acetate as the eluant to yield the desired product O-(3-bromophenyl) O-(4-cyano-6-methylfulfonylacridin-2-yl) S-phenyl phosphorothioate.

EXAMPLE 13

Preparation of O-(4-Fluorophenyl) O-(5-Methylsulfinylacridin-2-yl) S-(4-Nitrophenyl) Phosphorothioate 2-Hydroxy-5-methylsulfinylacridine (0.01 mole), triethylamine (0.01 mole), tetrahydrofuran (25 ml) and toluene (25 ml) are charged into a glass reaction vessel equipped with a mechanical stirrer and thermometer. The mixture is cooled to a temperature of about 0° C. and O-(4-fluorophenyl) S-(4-nitrophenyl) phosphorochloridothioate (0.01 mole) dissolved in toluene (25 ml) is added with stirring over a period of about 30 minutes. After the addition is completed the reaction mixture is allowed to warm to room temperature and stirring is continued for a period of about 16 hours. After this time the reaction mixture is filtered to remove triethylamine hydrochloride. The filtrate is then washed with water, dried over anhydrous magnesium sulfate and stripped of solvents leaving a residue. This residue is subjected to flash chromatography using ethyl acetate as the eluant to yield the desired product O-(4-fluorophenyl) O-(5-methylsulfinylacridin-2-yl) S-(4-nitrophenyl) phosphorothioate.

Additional compounds within the scope of the present invention which can be prepared by the procedures detailed in the foregoing examples are: O-ethyl O-butyl O-(5,6-dibromoacridin-2-yl) phosphate, O-propyl O-hexyl O-(7-fluoroacridin-3-yl) phosphate, O-butyl S-propyl O-(4-ethyl-7-cyanoacridin-3-yl) phosphorothioate, O-pentyl S-propyl O-(4,6-dipropylacridin-2-yl) phosphorothioate, O-hexyl S-propyl O-(7-hexylacridin-4-yl) phosphorothioate, O-(4-ethylphenyl) S-propyl O-(4-bromoacridin-2-yl) phosphorothioate, O-(3-propylphenyl) S-propyl O-(4-fluoroacridin-2-yl) phosphorothioate, O-(3-hexylphenyl) S-propyl O-(6-ethylsulfinylacridin-4-yl) phosphorothioate, O-(4-chloromethylphenyl) S-propyl O-(7-butylsulfinylacridin-4-yl) phosphorothioate, O-(2,4,6-trichlorophenyl) S-butyl O-(8-hexylsulfinylacridin-2-yl) phosphorothioate, O-ethyl S-pentyl O-(6-propylsulfonylacridin-2-yl) phosphorothioate, O-ethyl S-hexyl O-(6-pentylsulfonylacridin-3yl) phosphorothioate, O-ethyl S-butyl O-(4-propylsulfinylacridin-2-yl) phosphorothioate, O-ethyl S-propyl O-(4-hexylsulfonylacridin-1-yl) phosphorothioate, O-ethyl O-(4-fluoroacridin-2-yl) N,N-dimethylphosphoramidate, O-ethyl O-acridin-2-yl N-ethylphosphoramidate, O-ethyl O-acridin-3-yl N-butylphosphoramidate, O-ethyl O-acridon-4-yl N-hexylphosphoramidate, O-ethyl O-acridin-2-yl N,N-dibutylphosphoramidate, O-acridin-2-yl N,N-dimethyl(ethyl) phosphonamidate, O-acridin-3-yl N,N-diethyl(phenyl)phosphonamidate, O-acridin-4-yl N,N-diethyl(3-chlorophenyl)phosphonamidate, O-acridin-2-yl N,N-diethyl(4-methylphenyl)phosphonamidate.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophylite and the like. Granular formulations can be prepared by impregnating the compound, usually dissolved in a suitable solvent, onto and into granulated carriers such as the attapulgites or the vermiculites, usually of a particle size ranging from about 0.3 to 1.5 mm. Wettable powders, which can be dispersed in water and/or oil to any desired concentration of the active compound, can be prepared by incorporating wetting agents into concentrated dust compositions.

In some cases, the active compounds are sufficiently soluble in common organic solvents such as kerosene or xylene so that they can be used directly as solutions in these solvents. Frequently, solution of insecticides can be dispersed under superatmospheric pressure as aerosols. However, preferred liquid insecticidal compositions are emulsifiable concentrates which comprise an active compound according to this invention and as the inert carrier a solvent and an emulsifier. Such emulsifiable concentrates can be extended with water for application as sprays to the site of the insect infestation. The emulsifiers most commonly used in these concentrates are nonionic or mixtures of nonionic with anionic surface-active agents.

A typical insecticidal composition according to this invention is illustrated by the following example, in which the quantities are in parts by weight.

EXAMPLE 14

Preparation of a Dust

Product of Example 1: 10
Powdered Talc: 90

The above ingredients are mixed in a mechanical grinder-blender and are ground until a homogeneous, free-flowing dust of the desired particle size is obtained. This dust is suitable for direct application to the site of the insect infestation.

The compounds of this invention can be applied as insecticides in any manner recognized by the art. One method for destroying insects comprises applying to the locus of the infestation, an insecticidal composition comprising an inert carrier and, as the essential active ingredient, in a quantity which is toxic to said insects, a compound of the present invention. The concentration of the new compounds of this invention is the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to about 95 percent of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal composition to control insects, can include halogenated compounds such as DDT, methoxychlor, TDE, lindane, chlordane, isobenzan, aldrin, dieldrin, heptachlor, endrin, mirex, endosulfan, dicofol and the like; organic phosphorus compounds such as TEPP, schradan, ethion, parathion, EPN, demetron, carbophenothion phorate, zinophos, diazinon, malathion, mevinphos, dimethoate, DBD, ronnel, oxydemetro-methyl, dicapthon, chlorothion, phosphamidon, naled, fenthion, trichlorofon, DDVP, and the like; organic nitrogen compound such as dinitro-o-creson, dinitrocyclohexylphenol, DNB, DNP, binapacril, azobenzene and the like; organic sulfur compounds such as phenothiazine, phenoxathin, lauryl thiocyanate, bis(2-thiocyanoethyl)ether, isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like;

The compounds of the present invention can also be combined with fungicidal and nematocidal chemical compounds to form pesticidal compositions useful for the control of the fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like; while examples of nematocidal compounds are chloropicrin, O,O-diethyl O-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plant surfaces are taken up by the plant, and the insects are poisoned systematically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the woolly apple aphid, the Japanese, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for control of a light infestation of an insect under conditions unfavorable for its feeding while a pound or more of active compound per acre may be required for the control of a heavy infestation of insects under conditions favorable to their development.

The insecticidal activity of the compounds of the present invention was demonstrated by experiments carried out for the control of a variety of insects. In these experiments, the compounds to be tested are first put into a formulation suitable for application at various concentrations and application rates to plants and insects. The desired quantity of the test compound (the quantity being determined by the application concentration or application rate to be used in later testing) is dissolved or dispersed in a solvent consisting of acetone containing 3.19 grams/liter of Triton X-155 per liter.

Test plants used in these experiments are prepared by planting the appropriate seeds in sterilized soil contained in plastic pots having an upper soil surface area of approximately 12.25 square inches (aswuare pot having a 3.5 inch side). After the seed has been planted, a layer of approximately 0.25 inches of sand is spread on the top surface of the soil. The test compound is applied after the plant has reached a specified size.

For the foliar applications, the test compound, dissolved or dispersed in the water/acetone solvent described above, is sprayed as a mist onto the foliage of the test plants. The concentration of the test compound and the total quantity of solution applied is adjusted to give the application concentrations or rates desired, The plants are then allowed to air dry. Mites and aphids are exposed to treated leaves which have been left on the plant. Other insect species are exposed to treated leaves which have been removed from the plant and placed in petri dishes containing a piece of moist filter paper.

For the soil drench applications the test compound is first dissolved or dispersed in water/acetone as described above, then the amount of solution required to give a desired application rate is applied, using a pipette, evenly over the top of the soil in the pot. Twenty four hours after the treatment, mites and aphids are exposed to leaves which have been removed from the plants 24 hours after treatment and placed in petri dishes containing a piece of moist filter paper.

In direct contact applications, the test compound is, again, first formulated into a water/acetone solution, as described above, in the concentrations to be tested. Then the insect to be tested is dipped into, sprayed with or immersed in the liquid, dried, and observed for effect.

In the tables below setting forth the experimental data, PPM represents foliar application rates expressed as parts-per-million, #/A represents soil drench application rates expressed as pounds per acre.

CABBAGE LOOPER

Bush lima bean plants (Burpee Variety 222), two-leaf stage, are exposed, at various application rates, to the test compound applied as a foliar spray. Leaves are removed from the plants after approximately 30 minutes of air-drying of the foliar spray application, and placed in petri dishes containing a piece of moist filter paper. Ten cabbage loopers, second instar larval stage, are placed in each petri dish and the dish covered. Observations of insect mortality are made after 48 hours of exposure. Results of these tests are detailed in Table 1 below.

TABLE 1

| Test Compound | Application Rate: PPM | 256 | 128 | 64 | 32 | 16 |
|---|---|---|---|---|---|---|
| Product of Ex. 1 | | 100 | 100 | 100* | 90* | 70* |

NOTE:
* = Average of two tests

SOUTHERN ARMYWORM

Bush lima bean plants (Burpee Variety 222), two-leaf stage, are exposed, at various application rates, to the test compound applied as a foliar spray. Leaves are removed from the plants after approximately 30 minutes of air-drying of the foliar spray application and placed in petri dishes containing a piece of moist filter paper. Ten southern armyworms, second instar larval stage, are placed in each petri dish and the dish covered. Observations of insect mortality are made after 48 hours of exposure. Results of these tests are detailed in Table 2 below.

TABLE 2

| Test Compound | Application Rate: PPM | 256 | 128 | 64 | 32 | 16 |
|---|---|---|---|---|---|---|
| Product of Ex. 1 | | 100 | 100 | 100* | 85* | 45* |

NOTE:
* = Average of two tests

SOYBEAN LOOPER

Bush lima bean plants (Burpee Variety 222), two-leaf stage, are exposed, at various application rates, to the test compound applied as a foliar spray. Leaves are removed from the plants after approximately 30 minutes of air-drying of the foliar spray application and placed in petri dishes containing a piece of moist filter paper. Ten second instar larval soybean loopers are placed in each petri dish and the dish covered. Observations of insect mortality are made after 48 hours of exposure. Results of these tests are detailed in Table 3 below.

TABLE 3

| Test Compound | Application Rate: PPM | 256 | 128 | 64 | 32 | 16 |
|---|---|---|---|---|---|---|
| Product of Ex. 1 | | 100 | 100 | 90* | 60* | 40* |

NOTE:
* = Average of two tests

TOBACCO BUDWORM

Bush lima bean plants (Burpee Variety 222), two-leaf stage, are exposed, at various application rates, to the test compound applied as a foliar spray. Leaves are removed from the plants after approximately 30 minutes of air-drying of a foliar spray application and placed in petri dishes containing a piece of moist filter paper. Ten tobacco budworms, second instar larval stage, are placed in each petri dish and the dish covered. Observations of insect mortality are made after 48 hours of exposure. Results of these tests are detailed in Table 4 below.

TABLE 4

| Test Compound | Application Rate: PPM | 256 | 128 | 64 | 32 | 16 |
|---|---|---|---|---|---|---|
| Product of Ex. 1 | | 100 | 100 | 70* | 15* | 20* |

NOTE:
* = Average of two tests

MEXICAN BEAN BEETLE

Bush lima bean plants (Burpee Variety 222), two-leaf stage, are exposed, at various application rates, to the test compound applied as a foliar spray. Leaves are removed from the plants after approximately 30 minutes of air-drying of the foliar spray application and placed in petri dishes containing a piece of moist filter paper. Then mexican bean beetles, second instar larval stage, are placed in each petri dish and the dish covered. Observations of insect mortality are made after 48 hours of exposure. Results of these tests are detailed in Table 5 below.

TABLE 5

| Test Compound | Application Rate: PPM | 256 | 128 | 64 | 32 | 16 |
|---|---|---|---|---|---|---|
| Product of Ex. 1 | | 100 | — | — | — | — |

TWO-SPOTTED MITE

Bush lima bean plants (Burpee Variety 222) in the two-leaf stage are treated with the test compound, at various application rates, by the foliar spray method. The plants are air dryed for about 30 minutes after the foliar spray is applied, then 50–100 two-spotted mites, adults and nymphs, are put on each treated plant and on an untreated control plant by placing an untreated infested bean leaf containing 50–100 mites using the technique described above. An untreated control plant is similarly infested. After 48 hours of exposure of the insects to the treated plants, insect mortality is determined by comparison of the number of insects on the treated plants to the number on the untreated control plants. Results of this testing are set forth in Table 6 below.

TABLE 6

| Test Compound | Application Rate: PPM | 256 | 128 | 64 | 32 | 16 |
|---|---|---|---|---|---|---|
| Product of Ex. 1 | | 100 | — | — | — | — |

GERMAN COCKROACH

Solutions of test compounds are formulated as described hereinbefore and the solution which gives a desired application concentration is placed in a flask. Ten german cockroach adults are placed in a teaspoon test strainer and are dipped into the test solution. The excess solution is shaken off, the tea strainer opened and the insects placed in a clear plastic container containing a small moist piece of dental wick. The container is then capped with a cover pierced with air holes. Insect mortality is observed after 60 minutes, 24 hours and 48 hours following the exposure. Results of this testing are indicated in Table 7 below.

TABLE 7

| Test Compound | Application Rate: PPM | 256 | 128 | 64 | 32 |
|---|---|---|---|---|---|
| Product of Ex. 1 | (60) | 0 | — | — | — |
| | (24) | 100 | — | — | — |
| | (48) | 100 | — | — | — |

NOTE:
(60) = 60-minute mortality
(24) = 24-hour mortality
(48) = 48-hour mortality

SOUTHERN CORN ROOTWORM

A newly germinated corn seed is placed in a one-ounce plastic cup fitted with a snap-on plastic lid and covered with approximately 5 grams of sterilized soil. The test compound is formulated into solutions as described hereinbefore and applied to the soil as a soil drench at the desired application rates. After application the lids are snapped on the cups and the cups are allowed to stand for about 15 minutes to permit the solution to spread evenly through the soil. The lids are then removed, five second instar rootworm larvae are placed on the treated soil and the cups recapped. The cup is examined for insect mortality after 72 hours of exposure. Larvae which cannot crawl or right themselves are considered dead. Results of this testing are given in Table 8 below.

TABLE 8

| Test Compound | Application Rate: #/Acre | | | | | | |
|---|---|---|---|---|---|---|---|
| | 16 | 8 | 4 | 2 | 1 | .5 | .25 |
| Product of Ex. 1 | 90 | 65* | 65* | 50* | 40 | 50 | 40 |

NOTE:
* = Average of two tests

I claim:
1. A compound of the formula

$$\text{(I)}$$

wherein X and Y are each independently selected from the group consisting of halogen, alkyl of up to six carbon atoms, haloalkyl of up to six carbon atoms, nitro, alkylsulfinyl of up to six carbon atoms, alkylsulfonyl of up to six carbon atoms and cyano; m and n are integers from 0 to 1; $R^1$ is selected from the group consisting of alkyl of up to six carbon atoms and $$\text{(R}^3\text{)}_k$$

wherein $R^3$ is selected from the group consisting of halogen, alkyl of up to six carbon atoms, haloalkyl of up to six carbon atoms, nitro and cyano; and k is an integer from 0 to 3; $R^2$ is selected from the group consisting of alkyl of up to six carbon atoms, alkoxy of up to six carbon atoms, alkylthio of up to six carbon atoms, and $$\text{(R}^4\text{)}_t$$

wherein $R^4$ is selected from the group consisting of halogen, alkyl of up to six carbon atoms, haloalkyl of up to six carbon atoms, nitro and cyano; and t is an integer from 0 to 3; and A and B are each independently selected from the group consisting of oxygen and sulfur.

2. The compound of claim 1, O-ethyl O-acridin-2-yl S-propyl phosphorothioate.

3. The compound of claim 1, O-ethyl O-3-chloracridin-2-yl S-propyl phosphorothioate.

4. The compound of claim 1, O-methyl O-(4-chloroacridin-2-yl S-propyl phosphorothioate.

5. The compound of claim 1, O,O-diethyl O-(4-methylacridin-2-yl) phosphate.

6. The compound of claim 1, O-(3-chlorophenyl) O-(4,6-dichloroacridin-2-yl) methylphosphonate.

7. The compound of claim 1, O,S-diethyl O-(2-bromo-6-methylacridin-4-yl) phosphorothioate.

8. The compound of claim 1, O-(2,4-diethylphenyl) O-(6-trifluoromethylacridin-3-yl) S-propyl phosphorothioate.

9. An insecticidal composition comprising an inert carrier and, in a quantity toxic to insects, an effective amount of a compound of claim 1.

10. A method of insecticidally controlling insects which comprises contacting said insects or the locus of said insects with an insecticidal composition comprising an inert carrier and, in a quantity toxic to insects, an effective amount of a compound of claim 1.

* * * * *